US007351682B2

(12) United States Patent
Moaddel et al.

(10) Patent No.: US 7,351,682 B2
(45) **Date of Patent: *Apr. 1, 2008**

(54) MILD, LOW SOLUBLE SOAP BARS WHICH HAVE NON-SLIMY QUICK RINSE PERCEPTION IN USE

(75) Inventors: Teanoosh Moaddel, Bridgewater, NJ (US); Yury Yarovoy, Berkeley Heights, NJ (US); Michael Joseph Fair, Ridgewood, NJ (US); Georgia Shafer, West Caldwell, NJ (US); Christine Marie Nixon Lee, Fort Lee, NJ (US); Frank Meyer, Sao Paulo (BR)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/075,226

(22) Filed: Mar. 8, 2005

(65) Prior Publication Data

US 2006/0205620 A1 Sep. 14, 2006

(51) Int. Cl.
*A61K 7/50* (2006.01)

(52) U.S. Cl. ...................... 510/153; 510/152; 510/154; 510/155

(58) Field of Classification Search ..................... None
See application file for complete search history.

(56) References Cited

U.S. PATENT DOCUMENTS

| | | | | |
|---|---|---|---|---|
| 4,863,628 | A * | 9/1989 | Nambudiry | 510/130 |
| 5,076,953 | A * | 12/1991 | Jordan et al. | 510/151 |
| 5,703,025 | A * | 12/1997 | Zyngier et al. | 510/147 |
| 6,297,205 | B1 * | 10/2001 | Saxena et al. | 510/141 |
| 6,395,692 | B1 | 5/2002 | Jaworski et al. | |
| 6,537,953 | B2 * | 3/2003 | Schultz et al. | 510/152 |
| 6,689,728 | B2 * | 2/2004 | Diez | 510/147 |
| 6,846,786 | B1 | 1/2005 | Patel et al. | |
| 6,846,787 | B1 | 1/2005 | Farrell et al. | |
| 6,849,585 | B1 | 2/2005 | Farrell et al. | |

OTHER PUBLICATIONS

Copending, U.S. Appl. No. 10/883,326, filed Jul. 1, 2004, Morikis et al., Mild Synthetic Detergent Toilet Bar Compositon.

International Search Report Application No. PCT/EP2006/001444 mailed May 25, 2006.

* cited by examiner

*Primary Examiner*—Necholus Ogden
(74) *Attorney, Agent, or Firm*—Ronald A. Koatz

(57) ABSTRACT

The invention discloses bar compositions which are milder than soap but have squeaky feel or rinse associated with soap. This is accomplished by ensuring at least a certain portion (at least 1%), or all, of the soluble surfactant system is ion-sensitive. Further, soluble soap comprises less than 1% by wt. of bar, which helps produce a less alkaline pH bar while allowing squeaky feel to be produced.

6 Claims, No Drawings

MILD, LOW SOLUBLE SOAP BARS WHICH HAVE NON-SLIMY QUICK RINSE PERCEPTION IN USE

FIELD OF THE INVENTION

The present invention relates to cleansing bars which have low amount of soluble soap (and are preferably of relatively low pH), but are perceived as non-slimy/squeaky clean when rinsed from the skin or other substrate. The key is to utilize a soluble surfactant system (comprising less than 1% soluble soap), in addition to any insoluble surfactant present, wherein 1 to 100%, preferably 5 to 50%, more preferably 10 to 30% of the total soluble surfactant (principally synthetic) is calcium sensitive, said sensitivity defined by the surfactant forming a precipitate under water use conditions (French Hardness of 0.1 to 30, preferably 0.5 to 25, more preferably 1 to 15).

BACKGROUND

The present invention relates to a composition (preferably low pH composition of pH less than 7.5, more preferably less than 7.3, more preferably less than 7.1) which comprises both insoluble surfactant (e.g., insoluble soaps and insoluble synthetic, non-soap surfactants); and soluble surfactant (e.g., principally soluble synthetic, although the bar may comprise less than 1% soluble soap), yet have a squeaky, non-slimy rinse.

Generally, mild bars comprise synthetic surfactants, wherein the synthetic is used to alleviate harshness of pure soap or predominantly soap bar.

Although soap is harsh, it is also desirable to many consumers because the soap creates a feeling on the skin during rinse which has been described as "squeaky". This squeaky feeling drives a perception of cleanliness and, as noted, is desirable among soap consumers.

In an effort to maintain the mildness associated with synthetic surfactants, while at the same time providing the squeaky sensorial feel desirable to many consumers, applicants have noted that use of a soluble surfactant system (in addition to insoluble surfactant present), wherein at least a certain percentage of the total soluble system is calcium sensitive, results in bars which are both mild and perceptibly "squeaky".

Although there is not necessarily a direct correlation between low soluble surfactant and pH (i.e., other components in the bar composition also affect pH values), by minimizing or eliminating the use of soluble soap (i.e., so there is less than 1.0% by wt., preferably less than 0.5% by wt. total bar of soluble soaps), this helps to maintain pH of the bar composition lower so that it will have a pH of less than 7.5, preferably less than 7.3.

Stated differently, and without wishing to be bound by theory, when there is more available soluble soap, this soap will solubilize on dilution and can cause a higher pH. Insoluble soap, on the other hand, does not solubilize and is not available to raise pH. Thus, while as noted there are other compounds available which can raise pH in solution, minimizing or eliminating soluble soap altogether is an effective way to keep pH lower.

The surfactants and/or soap which are present and are not soluble in water (surfactant or soap of less than 1% solubility) will also not be calcium sensitive since they do not dissolve in water where the calcium ions will be available to interact.

In copending application, U.S. Ser. No. 10/883,326 to Morikis et al., entitled "Mild Synthetic Detergent Toilet Bar Composition", filed Jul. 1, 2004, applicants also seek to deliver squeaky sensation in a mild surfactant system. That application however uses 2% to 25% by wt. soluble soap (which has a tendency to raise pH); and uses ratios of components rather than predominantly calcium precipitated synthetic to provide the desired squeaky feel. Although pH may be lowered in other ways, Morikis et al. does not recognize the criticality of lower pH (i.e., pH below 7.5, preferably below 7.3, more preferably below 7.1) and typically has compositions with pH above 7.5.

Another co-pending U.S. application to Farrell et al., U.S. Ser. No. 10/756,615, filed Jan. 13, 2004, does not recognize that specific non-soap synthetic (i.e., those which are calcium sensitive and which precipitate under given hardness conditions) must be present in order to obtain the desired squeaky, non-slimy effect. The subject application is thus a clear selection over the disclosure of Farrell et al.

BRIEF DESCRIPTION OF THE INVENTION

Unexpectedly, applicants have found that mild, squeaky compositions can be produced using a soluble surfactant system having less than 1%, preferably less than 0.5% of soluble components soluble soap, wherein 1 to 100%, preferably 5 to 50%, more preferably 3 to 30% of the soluble components (soluble components are primarily the synthetic surfactant components) are calcium sensitive. By calcium sensitive is meant that the component (which is again predominantly synthetic surfactant since soluble soaps are minimized or absent) forms precipitate typically with divalent cations such as $Ca^{++}$ and $Mg^{++}$, at French Hardness of 0.1-30.

More specifically, the composition comprises:

(1) 7 to 75% by wt. of a surfactant system comprising:

(a) 5 to 30% by wt., preferably 7 to 25% by wt. of total composition of a component of said surfactant system wherein the component(s) are substantially insoluble in water (less than 1% solubility when measured in water at about 20° C.) and wherein said components comprise:

insoluble surfactants selected from the group consisting of anionic surfactants, nonionic surfactants, amphoteric surfactants, cationic surfactants, insoluble soap and mixtures thereof; and (b) 2 to 45% by wt. of total composition of a component(s) of said surfactant system wherein the components are soluble and wherein said component(s) comprise:

(i) less than 1% by wt. soluble soap;

(ii) 2% to 30%, preferably 5 to 25% total composition synthetic surfactant sensitive to precipitation by cations in water wherein water has French Hardness of 0.1 to 30, preferably 0.5 to 25, more preferably 1 to 15; and (iii) 0 to 15% total composition of synthetic surfactant which will not precipitate under same French Hardness conditions wherein 1 to 100%, preferably 5 to 50%, more preferably 10 to 30% of total soluble component (b) is sensitive to cation precipitation;

(2) 0 to 40%, preferably 5 to 35% by wt. of total composition insoluble free fatty acid (e.g., $C_{16}$ and up long chain fatty acids);

(3) 0 to 35%, preferably 5 to 30% by wt. of total composition water soluble structurants (e.g., PEG, glycerin); and (4) 4 to 14% by wt. of total composition water;

wherein said composition provides a squeaky, non-slimy rinse (e.g., of 11 or less, preferably 10.5 or less as measured in test defined in protocol).

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in Si units unless specified otherwise. All documents cited are—in relevant part—incorporated herein by reference.

DETAILED DESCRIPTION OF THE INVENTION

The present invention relates to bar compositions which are mild (such mildness provided, for example, because of use of synthetic surfactant), yet which have squeaky feel associated with soap (provided, for example, because at 1 to 100%, preferably 5 to 50% of the soluble surfactant present is calcium sensitive under use conditions).

In copending application Ser. No. 10/883,326 to Morikis et al., which applicants have filed on related subject matter, squeaky feel is obtained using certain amounts of soluble soap in combination with other criticalities relating to ratios of ingredients.

In the subject invention, the soluble components used to provide squeaky feel are primarily synthetic surfactants and less than 1% by wt. soluble soap is used. As discussed above, this both helps maintain lower pH of less than 7.5, preferably less than 7.3, while simultaneously providing compositions which are closer to skin pH and less irritating. Thus, squeaky feel is provided while still providing low irritation compositions.

Specifically, 1 to 100%, preferably 5 to 50%, more preferably 10 to 30% of the soluble surfactants (soluble surfactants are in total 2 to 45% of total composition) comprise surfactant which is sensitive to precipitation at French Hardness (FH) of 0.1-30. As noted, 5 to 30% by wt. of total composition comprises surfactant which is substantially insoluble (and therefore not sensitive to precipitation).

The ion-sensitive (e.g., sensitive to cation ions found in water) soluble surfactant, if used in combination with non ion-sensitive soluble surfactant, must comprise at least 1%, preferably 5 to 50% of the two and can comprise up to 100%. That is, it is required that there be at least a minimum amount of the ion-sensitive soluble surfactant. Generally, the ion-sensitive soluble surfactant will comprise 1-100%, preferably 5 to 50% more preferably 10 to 30% of the combination of sensitive and insensitive soluble surfactant.

The bars of the invention also comprise a non-soluble surfactant portion which can be non soluble soap (e.g., alkali metal stearate) or non-soluble synthetic surfactant. As for the soluble surfactant, this soluble surfactant portion is distinguished over the art at least in that 99% or more of said soluble surfactant in composition of the subject invention comprises synthetic (i.e., non-soap) surfactant.

In addition to surfactant, compositions of the invention, preferably comprise free fatty acid (acting, for example, to buffer pH and/or act as structurant), water soluble structurant (PEG, glycerin) and water.

The application is discussed in greater below.

Surfactant System

The surfactant system of the invention comprises really two parts: (1) insoluble surfactant such as alkali metal, long chain (preferably $C_{16}$ to $C_{24}$) fatty acid soaps (e.g., sodium stearate) and/or insoluble synthetic surfactant; and (2) soluble surfactant (soluble soaps may not comprise more than 1% by wt. of total bar composition). Within the group of soluble surfactants (primarily or entirely synthetic), some surfactants are more sensitive than others to ion (primarily calcium) precipitation.

Applicants have found that using little or no soluble soap and soluble surfactants, wherein at least 1% of all soluble components are sensitive to water hardness, affects the consumer perception of squeakiness. More specifically, applicants have found that the proper balance of compounds allow bars to be made which will both be considered adequately mild by the consumer (e.g., relative to predominantly soap bar), and yet which will provide the "squeaky" clean feel which consumers associate with soap.

The key to the invention is to formulate the soluble surfactant component so that at least a minimum amount of the soluble surfactant (e.g., 1% of total soluble surfactant up to 100% of total soluble surfactant, preferably 5 to 50%) is sensitive to calcium and other divalent cations (e.g., $Ca^{+2}$ and $Mg^{+2}$ found in water).

Thus, the overall surfactant system comprises 7 to 75% by wt., preferably 15 to 65% by wt., more preferably 25 to 65% by wt. of the bar, where 5 to 30% by wt., preferably 7 to 25% by wt. of total composition comprises insoluble fatty acid soap and/or other insoluble surfactants; and 2 to 45%, preferably 5 to 35% by wt. of total composition comprises soluble surfactant comprising water soluble soap (although no more than 1% by wt. of total bar) and mixture of divalent cation sensitive and divalent cation insensitive synthetic surfactant (i.e., synthetic comprises at least about 99% of soluble surfactant). Within the soluble surfactant system, at least 1% to 100% of total soluble surfactant, preferably at least 5 to 50% of soluble surfactant must be divalent cation sensitive.

As noted, insoluble surfactant comprises insoluble fatty acid soap. This includes soaps of $C_{16}$-$C_{24}$ fatty acids such as, for example, alkali metal palmitate or alkali metal stearate. The insoluble surfactant may also include insoluble synthetic surfactant The soluble surfactant may be a soluble soap such as $C_8$-$C_{14}$ fatty acid soap. However, the soluble soap may comprise no more than 1% by wt. of bar.

The soluble surfactant comprises predominantly (at least 99% soluble surfactant) synthetic surfactant and such synthetic may be divided into two classes, ion sensitive soluble synthetic and ion-insensitive soluble synthetic.

The insensitive component is optional (0 to 15% by wt. total composition), although it will generally comprise 1 to 10% of the bar composition. Sensitivity or insensitivity generally is measured with regard to calcium ions present in the water during rinse. By insensitive is meant generally that, in water of French Hardness of 6 (60 ppm calcium in water), the surfactant will not precipitate with the calcium and surfactant micelles (believed responsible for "slimy" rather than "squeaky" feel) will remain generally intact. Conversely, ion sensitive surfactants, under same conditions, will tend to lose their micellar formation to yield desired "squeaky" feel. Examples of soluble, but insensitive, synthetics include acyl isethionate (e.g., sodium cocoyl isethionate), alkyl sulphate (e.g., sodium dodecyl sulphate), alkyl ether sulfate, alkyl sulfosuccinate (e.g., cocoamidosulfosuccinate), and certain amphoterics (e.g., betaine).

Examples of surfactants sensitive to precipitation include salts of alkyl carboxylate acids (e.g., soaps); carboxylates of formula:

$$R-(CH_2CH_2O)_nCO_2M$$

wherein R ranges from $C_8$-$C_{20}$ alkyl, preferably $C_{12}$-$C_{18}$ alkyl, n is from 1 to 40, preferably 2 to 9, and M is sodium, potassium, ammonium or triethanolammonium; carboxylate salts of fatty acyl amino acids (e.g., sodium cocoyl glycinate, sodium lauryoy lactylate); monoalkyl phosphates; and certain types of amphoterics (e.g., n-alkyl iminodialkanoate).

As noted, certain categories may overlap; however sensitivity/insensitivity is measured by French Hardness, as noted above, and is the determinative factor in deciding what to use.

Other Components

Compositions of the invention further contain 0 to 40%, preferably 5 to 35% by wt. total composition free fatty acid. Generally at least some free fatty acid is needed to act as pH buffer (keep pH lower) as well as structurant.

Importantly, any free fatty acid present is also long chain, insoluble free fatty acid. For example, the free fatty acid may be $C_{16}$-$C_{24}$ free fatty acid. Typically, it will comprise mixtures of $C_{16}$ and $C_{18}$ (e.g., palmitic/stearic acid mixtures).

The bar may comprise water-soluble polymers to assist in structuring the bars. These may include relatively shorter chain polyalkylene glycols such as PEG-80 or glycerin molecules. It may further include water soluble molecules chemically modified with hydrophobic moiety or moieties, for example, EO-PO block copolymer, hydrophobically modified PEGs (e.g., POE (200)-glyceryl-stearate, PEG-150 stearate etc.). Typically, these water-soluble structurants are present at level of 0-35%, preferably 5 to 30% of bar composition.

A preferred composition has ratio of 25:75 to 75:25 polyalkylene glycol to glycerin, preferably 40:60 to 60:40 ratio.

Typically, bar compositions will further comprise 2-20%, preferably 4 to 12% by wt. total composition water.

In addition, the bar compositions of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers which may be used include Quatrisoft LM-200 Polyquaternium-24, Merquat Plus 3330-Polyquaternium 39; and Jaguar® type conditioners.

Another ingredient which may be included are exfoliants such as polyoxyethylene beads, walnut shells and apricot seeds.

The present invention is set forth in greater detail in the examples which follow. The examples are for illustration purposes only and are not intended to limit the scope of the claims in any way.

All percentages in the examples and specification, unless indicated otherwise are intended to be percentages by weight.

An important aspect of the bars of the invention is that the pH of the bars is below 7.5, preferably below 7.3, more preferably below 7.1.

It is completely unexpected that inclusion of at least certain amount (i.e., at least 1% of soluble component) of ion-sensitive component into the soluble-surfactant system will provide squeaky feel while maintaining good mildness, especially since it facilitates making a bar with pH below 7.5, preferably below 7.3 while allowing a way to obtain the squeaky feel.

In preferred embodiments of the invention, squeaky feel, according to test conducted by trained evaluating panelists, is 11 or less, preferably 10.5 or less, more preferably 10 or less; or more preferably 9.5 or less.

EXAMPLES

Protocol

Protocol for evaluation of squeakiness (i.e., less slimy the feel, the more squeaky the feel) for bar formulations:

Wash hands before you begin

Splash face 3 times with running water;

Pick up implement;

Wet implement under running water (about 10 seconds);

Pick up dry bar

Place dry bar under running water (about 5 seconds);

Rub wet bar against implement 5 time in a downward motion

Put bar down;

Begin to rub implement with hands for a count of 10 times;

Put implement down

Begin to work lather 1 2 3 4 5 6 7 8 9 10; Pick up lather 2 times

Repeat this procedure 2 more times

Lather should be worked in a fast whipping motion.

Rub hands together or a count of 1 2 3 4 5; Fold over 1 2 3 4 5

Fold over (i.e., turn over lather generated after rubbing)

Continue with half face wash design as follows.

Put bubbles from lather generated above on half of face (e.g., left side);

Begin to wash half face—1 2 3 4 5 6 7 8; Repeat 1 2 3 4 5 6 7 8;

When washing—begin at the chin, work up to forehead and work down again—repeat 2 times;

Rinse hands under running water five times;

Begin to rinse face 1 2 3 4 5, evaluate (how fast lather rinsed off) 6 7 8 9 10, and evaluate sliminess left on the skin on a 36 point scale at after 10 rubs;

Pat dry;

The evaluation is based on a scale wherein score of 36 is judged to be least squeaky and most slimy (typically based on bar having greater than 40%, preferably greater than 50% sodium isethionate); and 1 is judged to be most squeaky and least slimy (typically a bar where surfactant is greater than 95, preferably greater than 98% soap). About 16-24 panelists are used and score is averaged across panelists.

Specifically, the control bar (used on half the face) is a squeaky bar (which panelists have previously evaluated and established a control score of about 8.61±0.81; this score is marked for their reference on the scale so panelists know where it sits) and is used on half the face according to procedure noted above. The panelists then use a "test" bar on the other side of face (using same procedure as described above) and are asked to evaluate on a scale of 1-36 against the control bar (again, as noted, which has been marked on the scale for their reference).

The evaluation scale is actually an evaluation of perceived "sliminess". Since the perceived sliminess is inversely proportional to the perceived "squeakiness", the lower the score on the sliminess scale (closer or below to value of 8.61 used for control), the better the squeakiness (desired value).

Definition of French Hardness

1 French Hardness Unit is equal to 10 parts per million of ion, as $CaCO_3$. This is defined, for example, in "The Water Encyclopedia", 2nd Edition, Fritz van der Leeden et al. Lewis Publishers, Inc. (1990).

Examples 1 and 2 and Comparative A

In order to show effect of minimum amount of sensitive soluble surfactant relative to not having soluble sensitive surfactant, applicants prepared the following examples.

| Ingredient | Example 1 (MAP) % by wt. | Example 2 (lactylate) % by wt. | Comparative A % by wt. |
|---|---|---|---|
| Free fatty acid (palmitic acid/stearic acid) | 25.76 | 25.76 | 25.76 |
| Cocoamidosulfosuccinate (insensitive soluble) | 5.66 | 5.66 | 22.66 |
| Sodium monoalkyl phosphate (MAP) | 17.00 | — | — |
| Sodium lauroyl lactylate | — | 17.00 | |
| Sodium soap[1] | 16.20 | 16.20 | 16.20 |
| PEG 8000 | 13.81 | 13.81 | 13.81 |
| Glycerin | 13.81 | 13.81 | 13.81 |
| Fragrance | 1.00 | 1.00 | 1.00 |
| $TiO_2$ | 0.75 | 0.75 | 0.75 |
| EDTA | 0.02 | 0.02 | 0.02 |
| HDPA | 0.02 | 0.02 | 0.02 |
| Water | ≈6.67 | ≈6.67 | ≈6.67 |

[1]The soap here is part of the substantially insoluble component (as defined in the text above).

Using the application protocol noted above, the compositions proposed were tested for perceived squeakiness (as indicated, test was actually for sliminess and squeakiness is inversely related, i.e., lower the sliminess, greater the squeakiness) and results were set forth in the Table below.

Perceived Squeakiness—Perceived Squeakiness Value on "Sliminess" Scale

| | |
|---|---|
| Example 1 | 5.82 ± .57 |
| Example 2 | 9.0 ± .57 |
| Comparative | 11.53 ± .59 |

As noted, examples of invention had lower "slimy" scores, associated with enhanced squeakiness.

As clearly seen from the table, when soluble surfactant (CAS & MAP; CAS and Lactylate; or CAS alone) is sensitive in hard water (as are MAP and lactylate) and these comprise at least 1% of soluble surfactants, perceived sliminess value are driven low (i.e., squeakiness effect is perceived better), even though the bars are mild (e.g., per low pH), unlike pure soap bars (which are squeaky).

In this regard, it is noted that a pure soap bar had score of 8.61±0.81, although such pure soap bar would be considered much harsher (more irritating to skin because of pH) than a bar with synthetic. The tested soap bar had the following formulations:

| Ingredient | % by wt. |
|---|---|
| Anhydrous 65/35 soap | 77.25 |
| Palm Kernel Oil Fatty Acid | 7.50 |
| Water | 13.50 |
| Fragrance | 4.00 |
| $TiO_2$ | 0.75 |
| pH | 9-10 |

The invention claimed is:

1. Bar composition comprising:

(1) 7 to 75% by wt. of a surfactant system comprising:

(a) 5 to 30% by wt. total composition of a component of said surfactant system wherein the component(s) are substantially insoluble in water, less than 1% solubility when measured in water at about 20° C., and wherein said components comprise:

(i) about 16.2% by wt. insoluble alkali metal fatty acid soap; and (ii) about 5.66% by wt. of amido sulfosuccinate; and (b) 2 to 45% by wt. total composition of a component(s) of said surfactant system wherein the components are soluble and wherein said components comprise:

(i) less than 1% by wt. soluble soap;

(ii) about 17% by wt. of a surfactant selected from the group consisting of monoalkyl phosphate, alkoyl lactylate and mixtures thereof which surfactant(s) is sensitive to precipitation by ions in water having French Hardness of 0.1 to 30; and (2) 5 to 35% by wt. total composition of insoluble $C_{16}$ to $C_{24}$ free fatty acid;

(3) 5 to 35% by wt. total composition water soluble structurants wherein said structurants comprise structurants selected from the group consisting of alkylene glycol, glycerin and mixtures thereof; and (4) 4 to 14% by wt. total composition water;

wherein composition has pH of less than 7.5; and wherein the composition has a squeaky, non-slimy rinse value of 11 or less.

2. A composition according to claim 1, wherein surfactant system comprises 15-65% by wt. of total bar.

3. A composition according to claim 1, wherein insoluble compound (a) comprises 7% to 25% by wt. total composition.

4. A composition according to claim 1, wherein said water soluble structurant of (3) comprises both alkylene glycol and glycerin, and wherein the ratio of alkylene glycol to glycerin is 75:25 to 25:75.

5. A composition according to claim 1, wherein said composition has squeaky, non-slimy rinse of 10.5 or less.

6. A composition according to claim 5, wherein said composition has squeaky, non-slimy rinse of 10 or less.

* * * * *